United States Patent
Mounier et al.

(10) Patent No.: US 10,683,545 B2
(45) Date of Patent: Jun. 16, 2020

(54) MICRORNAS CHARACTERIZING ACNE AND THE USES THEREOF

(71) Applicant: GALDERMA RESEARCH & DEVELOPMENT, Biot (FR)

(72) Inventors: Carine Mounier, Valbonne (FR); Sophie Deret, Mougins (FR)

(73) Assignee: GALDERMA RESEARCH & DEVELOPMENT, Boit (FR)

( * ) Notice: Subject to any disclaimer, the term of this patent is extended or adjusted under 35 U.S.C. 154(b) by 0 days.

(21) Appl. No.: 15/502,418

(22) PCT Filed: Aug. 6, 2015

(86) PCT No.: PCT/FR2015/052172
§ 371 (c)(1),
(2) Date: Feb. 7, 2017

(87) PCT Pub. No.: WO2016/020626
PCT Pub. Date: Feb. 11, 2016

(65) Prior Publication Data
US 2017/0226587 A1    Aug. 10, 2017

(30) Foreign Application Priority Data

Aug. 7, 2014   (FR) ..................................... 14 57669

(51) Int. Cl.
*C12Q 1/68*     (2018.01)
*C12Q 1/6883*   (2018.01)

(52) U.S. Cl.
CPC ..... *C12Q 1/6883* (2013.01); *C12Q 2600/106* (2013.01); *C12Q 2600/118* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2001/0051344 A1* | 12/2001 | Shalon | B01L 3/0244 435/6.11 |
| 2007/0161004 A1* | 7/2007 | Brown | C12N 15/111 435/6.14 |
| 2012/0259000 A1 | 10/2012 | Marionnet et al. | |

FOREIGN PATENT DOCUMENTS

| | | |
|---|---|---|
| WO | 2005118806 A2 | 12/2005 |
| WO | 2011053257 A2 | 5/2011 |

OTHER PUBLICATIONS

Enard et al. (Science 2002. vol. 296 p. 340) (Year: 2002).*
Cobb et al (Crit Care Med 2002 vol. 30 p. 2711) (Year: 2002).*
Lucentini (The Scientist, 2004, vol. 18, p. 20) (Year: 2004).*
International Search Report dated Nov. 4, 2015 corresponding to International Patent Application No. PCT/FR2015/052172, 6 pages.
Genechip: "Data Sheet GeneChip TM miRNA 3.0 Array," Mar. 2012, XP055222758 [retrieved from the Internet on Oct. 21, 2015], 4 pages.

* cited by examiner

*Primary Examiner* — Katherine D Salmon
(74) *Attorney, Agent, or Firm* — Sunit Talapatra; Foley & Lardner LLP

(57) ABSTRACT

The invention relates to the identification of microRNAs associated with acne and to the use thereof.

7 Claims, No Drawings

MICRORNAS CHARACTERIZING ACNE AND THE USES THEREOF

CROSS-REFERENCE TO PRIOR APPLICATIONS

This application is a National Stage of PCT/FR2015/052172, filed Aug. 6, 2015, and designating the United States (published on Feb. 11, 2016, as WO 2016/020626 A1), which claims priority under 35 U.S.C. § 119 to French Application No. 1457669, filed Aug. 7, 2014, each hereby expressly incorporated by reference in its entirety and each assigned to the assignee hereof.

The present invention relates to the field of medicine and more particularly to the diagnosis and the treatment of acne.

PRIOR ART

Acne is a common multifactorial pathology which affects skin rich in sebaceous glands (face, scapular region, arms and intertriginous areas). It is the most common form of dermatosis. The following pathogenic factors play a determining role in acne formation: genetic predisposition, sebum overproduction (seborrhea), androgens, follicular keratinization disorders (comedogenesis) and bacterial colonization and inflammatory factors.

Several forms of acne exist, all having in common that the pilosebaceous follicles are attacked. Examples include acne conglobata, acne keloidalis nuchae, drug-induced acne, recurrent acne miliaris, acne necrotica, acne neonatorum, premenstrual acne, occupational acne, senile acne, solar acne and acne vulgaris.

Acne vulgaris, also known as polymorphous juvenile acne, is the most common form. It comprises four stages, but it is not necessary to pass through every stage:

- Stage 1 corresponds to comedonal acne, characterized by a large number of open and/or closed comedones and of microcysts.
- Stage 2, or papulopustular acne, is mildly to moderately serious. It is characterized by the presence of open and/or closed comedones and of microcysts, but also of red papules and of pustules. It mainly affects the face and leaves few scars.
- Stage 3, or papulocomedonal acne, is more serious and extends to the back, the thorax and shoulders. It is accompanied by a greater number of scars.
- Stage 4, or nodulocystic acne, is accompanied by numerous scars. It exhibits nodules and large painful purplish pustules.

The various forms of acne described above can be treated with active agents such as anti-seborrheics and anti-infectives, for example benzoyl peroxide (particularly the product Eclaran® marketed by Pierre Fabre), with retinoids such as tretinoin (particularly the product Retacnyl® marketed by Galderma) or isotretinoin (the product Roaccutane® marketed by Laboratoires Roche), or with naphthoic acid derivatives. Naphthoic acid derivatives such as in particular 6-[3-(1-adamantyl)-4-methoxyphenyl]-2-naphthoic) acid, commonly called adapalene (the product Differin® marketed by Galderma), are widely described and recognized as active agents which are as effective as tretinoin for treating acne.

The combination of several local treatments (antibiotics, retinoids, peroxides, zinc) is also used in dermatology to increase the efficiency of active agents and to decrease their toxicity (Cunliffe W. J., *J. Dermatol. Treat.*, 2000, 11 (suppl. 2), S13-S14).

The multiple application of different dermatological products may be quite burdensome and demanding for the patient.

Thus, any new means of diagnosis or prognosis or any new tool for screening or analyzing patient populations is extremely useful.

SUMMARY OF THE INVENTION

The present invention is based on the identification of microRNAs which are differentially expressed in subjects suffering from acne.

The invention is directed more precisely at all the following microRNAs: hsa-miR-223, hsa-miR-21*, hsa-miR-212, hsa-miR-21, hsa-miR-421, hsa-miR-29b-1*, hsa-miR-146b-5p, hsa-miR-146b-3p, hsa-miR-941, hsa-miR-27a* and hsa-miR-155, as biomarkers of acne.

These microRNAs are useful as biomarkers for diagnosing acne, for screening molecules that can be used to treat acne, or for determining the efficacy of an acne treatment.

The present invention provides a method for diagnosing acne in a subject, comprising determining in a sample from said subject the expression of all the following microRNAs: hsa-miR-223, hsa-miR-21*, hsa-miR-212, hsa-miR-21, hsa-miR-421, hsa-miR-29b-1*, hsa-miR-146b-5p, hsa-miR-146b-3p, hsa-miR-941, hsa-miR-27a* and hsa-miR-155.

DESCRIPTION OF THE INVENTION

Definitions

MicroRNAs

MicroRNAs are small non-coding RNAs of 18 to 25 nucleotides, expressed in most eukaryotic organisms, which play an important role in the regulation of gene expression. These are powerful post-transcriptional repressors: by binding by complementarity to specific nucleotide sequences present on mRNAs, they prevent these so-called "target" transcripts from being translated into proteins. A microRNA has several target mRNAs and, conversely, an mRNA is the target of several microRNAs.

All known microRNAs are listed in the miRBase database (miRBase, http://www.mirbase.org). Homologous microRNAs can be found in several organisms; an annotation system has thus been set up to assign a single identifier thereto. MicroRNAs are identified by a number preceded by the abbreviation "miR" or "mir", which allows a distinction between the mature microRNA (miR) and the stem-loop structure of the microRNA precursor (mir). A prefix is used to distinguish between species, such as, for example, hsa-miR-101 and mmu-miR-101 to distinguish between the human microRNA (hsa: *Homo sapiens*) and the mouse microRNA (mmu: *Mus musculus*). In certain cases, the same stem-loop precursor can give rise to the synthesis of two different microRNAs. The annotation system allows a distinction between these two microRNAs: the microRNA from the 5' side of the loop is denoted 5p and the microRNA from the 3' side is denoted 3p. This 3p and 5p annotation is used until the abundance of one of the two forms is determined. The majority form "miR-xxx" is then distinguished from the minority form "miR-xxx*".

MicroRNAs are involved in a wide range of key biological processes, such as cell cycle control and apoptosis. They also regulate several physiological and developmental processes, such as stem cell differentiation, hematopoiesis, hypoxia, muscle development, neurogenesis, insulin secretion, cholesterol metabolism, aging and immune and inflammatory responses. Moreover, distinct patterns of temporal expression during embryogenesis and tissue-specific expression profiles suggest that microRNAs play an essential role in tissue differentiation and maintenance of identity. These biological processes are often dysregulated in affected individuals. Numerous studies have shown the involvement of microRNAs in certain pathologies, including various cancers, cardiac diseases and neurological disorders. More recently, the role of microRNAs was also shown in certain dermatological diseases such as psoriasis, vitiligo and certain skin cancers.

Subjects

The subjects are human patients, men or women, of any age.

Biological Samples

The samples tested are typically samples of dermis, of epidermis or of dermis and epidermis. In certain embodiments, it is a skin biopsy, preferably taken from affected regions of the skin. More specifically, they are preferably skin biopsies from lesional areas, for example bearing papules.

It may also be any sample of biological fluid, such as blood, saliva or urine.

Controls

The "control" samples, or the "control" expression levels, are samples, or expression levels, from healthy subjects or subjects having another pathology, potentially another skin pathology.

Diagnostic Applications

The present invention relates to the identification of microRNAs and/or precursors thereof which are differentially expressed in subjects suffering from acne compared with healthy subjects or subjects having another skin pathology, such as rosacea, particularly type II rosacea.

Based on the identified microRNAs, it is possible to:
use these microRNAs as biomarkers of acne;
use one or more identified microRNAs for the diagnosis, detection, stage determination, monitoring and prognosis of acne;
carry out a method of diagnosis, detection, stage determination, monitoring and prognosis of acne, the method comprising at least one step of determining the expression level of one or more identified microRNAs in a patient sample;
prepare a kit for the diagnosis, detection, stage determination, monitoring and prognosis of acne, the kit comprising means for detecting the expression level of one or more identified microRNAs. Preferably, the detection means are nucleic acids or peptides having a capacity to bind to one or more identified microRNAs, preferably specific oligonucleotides or probes of one or more identified microRNAs;
use these microRNAs to perform population or cluster analyses, for example to differentiate subjects suffering from acne and healthy subjects.

Once the diagnosis is made, an acne treatment can be envisaged.

The method for diagnosing acne in a subject according to the invention comprises determining in a sample from said subject the expression of all the following microRNAs: hsa-miR-223, hsa-miR-21*, hsa-miR-212, hsa-miR-21, hsa-miR-421, hsa-miR-29b-1*, hsa-miR-146b-5p, hsa-miR-146b-3p, hsa-miR-941, hsa-miR-27a* and hsa-miR-155.

Advantageously, an increase in the expression of these microRNAs in the sample relative to controls indicates that the subject suffers from or is likely to suffer from acne.

In a particular embodiment, the method further includes additionally determining in a sample from said subject the expression of at least one microRNA selected from the group consisting of hsa-miR-617, hsa-miR-885-5p, hsa-miR-652, hsa-miR-1281, hsa-miR-4310, hsa-miR-4800-3p, hsa-miR-4727-3p, hsa-miR-4791, hsa-miR-505*, hsa-miR-3651, hsa-miR-543, hsa-miR-23a*, hsa-miR-18a, hsa-miR-1246, hsa-miR-3615, hsa-miR-4484, hsa-miR-4800-5p, hsa-miR-629*, hsa-miR-30e*, hsa-miR-24-2*, hsa-miR-18b, hsa-miR-4667-5p, hsa-miR-483-5p, hsa-miR-27b*, hsa-miR-629, hsa-miR-187, hsa-miR-487a, hsa-miR-1244, hsa-miR-132, hsa-miR-550a*, hsa-miR-4286, hsa-miR-542-5p, hsa-let-7i*, hsa-miR-625, hsa-miR-411, hsa-miR-3175, hsa-miR-192, hsa-miR-503, hsa-miR-31, hsa-miR-1301 hsa-miR-92a-1*, hsa-miR-501-5p, hsa-miR-4732-5p, hsa-miR-150, hsa-miR-424*, hsa-miR-4417, hsa-miR-4521, hsa-miR-365* and hsa-miR-181a*.

According to a preferred aspect, the method comprises additionally determining in a sample from said subject the expression of one or more microRNAs selected from the group consisting of hsa-miR-617, hsa-miR-885-5p, hsa-miR-652, hsa-miR-1281, hsa-miR-4310, hsa-miR-4800-3p, hsa-miR-4727-3p and hsa-miR-4791, wherein a decrease in the expression of one or more of these microRNAs in the sample relative to controls indicates that the subject suffers from or is likely to suffer from acne.

According to another aspect, the method comprises additionally determining in a sample from said subject the expression of one or more microRNAs selected from the group consisting of hsa-miR-505*, hsa-miR-3651, hsa-miR-543, hsa-miR-23a*, hsa-miR-18a, hsa-miR-1246, hsa-miR-3615, hsa-miR-4484, hsa-miR-4800-5p, hsa-miR-629*, hsa-miR-30e*, hsa-miR-24-2*, hsa-miR-18b, hsa-miR-4667-5p, hsa-miR-483-5p, hsa-miR-27b*, hsa-miR-629, hsa-miR-187, hsa-miR-487a, hsa-miR-1244, hsa-miR-132, hsa-miR-550a*, hsa-miR-4286, hsa-miR-542-5p, hsa-let-7i*, hsa-miR-625, hsa-miR-411, hsa-miR-3175, hsa-miR-192, hsa-miR-503, hsa-miR-31, hsa-miR-1301 hsa-miR-92a-1*, hsa-miR-501-5p, hsa-miR-4732-5p, hsa-miR-150, hsa-miR-424*, hsa-miR-4417, hsa-miR-4521, hsa-miR-365*, hsa-miR-181a*, hsa-miR-155, hsa-miR-27a*, hsa-miR-941, hsa-miR-146b-3p, hsa-miR-146b-5p, hsa-miR-29b-1*, hsa-miR-421, hsa-miR-21, hsa-miR-212, hsa-miR-21* and hsa-miR-223.

The invention also provides a kit comprising means for specifically detecting the following microRNAs: hsa-miR-223, hsa-miR-21*, hsa-miR-212, hsa-miR-21, hsa-miR-421, hsa-miR-29b-1*, hsa-miR-146b-5p, hsa-miR-146b-3p, hsa-miR-941, hsa-miR-27a* and hsa-miR-155, preferably specific probes or primers.

The detection or the quantification of the biological sample(s) from the control subject(s) may be concomitant with those carried out for the patient sample or may come from data collected earlier and available, for example, in a database.

In the methods according to the invention, microRNA expression may be detected or quantified according to methods well known to persons skilled in the art, for example by quantitative RT-PCR and/or hybridization techniques, for example using a labeled probe or a chip.

Based on the identified microRNAs, it is further possible to carry out a method for monitoring the therapeutic efficacy of a treatment wherein a step of determining the expression level of one or more of the identified microRNAs in a patient sample is carried out before, during and/or after treatment and the expression levels are compared.

Therapeutic Applications

It is also possible to target the regulation of these microRNAs to treat or prevent acne; the molecule used for the treatment is a molecule allowing to decrease or suppress dysregulation of the expression of one or more microRNAs differentially expressed in subjects suffering from acne. In particular, microRNAs underexpressed in subjects suffering from acne may be used to treat acne by administering same. Alternatively, when microRNAs are overexpressed in subjects suffering from acne, the treatment will be directed at increasing the expression of the target gene, for example by blocking the effect of these microRNAs.

Described herein is a pharmaceutical composition comprising one or more identified microRNAs or precursors thereof and the use of same to treat acne or to prepare a drug intended to treat acne. Preferably, the composition further includes one or more pharmaceutically acceptable excipients and/or carriers. The present invention also relates to an expression vector comprising a nucleotide sequence encoding one or more identified microRNAs or precursors thereof and the use of same to treat acne or to prepare a drug intended to treat acne. Preferably, the identified microRNAs are selected from microRNAs underexpressed in patients suffering from acne. Preferably, the pharmaceutical composition is a dermatological composition. In particular, the composition is intended for topical administration.

Also described is the use in the treatment of acne of a molecule or a combination of molecules, said molecule or combination of molecules allowing to increase or decrease the expression or the activity of one or more microRNAs described herein.

According to a particular aspect, said molecule or combination of molecules is one or more of the microRNAs described herein, or precursors of these microRNAs, or is a nucleic acid encoding said microRNA(s) or precursors thereof, or is an analog, derivative or modified form of the microRNA(s) retaining its or their activity.

According to another aspect, the molecule or combination of molecules is an inhibitor of the microRNA(s), preferably a sense or antisense oligonucleotide capable of hybridizing to said microRNA(s), thus inhibiting the production and/or the activity of the microRNA(s) or increasing the depletion of the microRNA(s).

It is also envisaged to perform a screening to identify novel drugs for treating acne, wherein candidate molecules will be tested as to their capacity to fully or partially restore the expression of dysregulated microRNAs in subjects suffering from acne and the molecules having the desired effect will be selected.

Thus described is a method for screening molecules useful in the treatment of acne, comprising a) contacting a cell with a test molecule, b) determining the expression of one or more microRNAs as described herein and c) selecting the test molecule if it increases or decreases the expression or the activity of one or more of said microRNAs.

Typically, the expression of a microRNA is analyzed and compared in the presence and in the absence of the test molecule.

The following experimental section illustrates the invention without limiting its scope.

Examples

Introduction

The present invention relates to the identification of 60 microRNAs and/or precursors thereof which are differentially expressed in subjects suffering from acne compared with healthy subjects.

The miRNome was characterized in acneic lesional skin versus non-lesional skin. Eleven subjects were studied with, for each subject, one biopsy from the back (non-lesional skin) and one biopsy from the back in a lesional region (papule).

To carry the characterization of the pathology's miRNome through to a successful conclusion, a large-scale study was undertaken, using Affymetrix miRNA 3.0 chips, to establish microRNA expression profiles.

Results

Large-Scale Study of microRNAs

The present analysis identified 60 microRNAs differentially expressed in acneic lesional skin (LS) versus non-lesional skin (NLS).

TABLE 1

List of the 60 modulated mature microRNAs (|fold| ≥ 1.5 and raw p-value ≤ 0.05) in LS vs NLS differential analysis (Blume acne study: GRDS0051) starting with 3391 Affymetrix identifiers

| Affymetrix id | Fold Change | RawPValue | FDR_BH | mean expression LS | mean expression NLS |
|---|---|---|---|---|---|
| hsa-miR-617 | −2.1 | 2.4E−02 | 4.8E−01 | 6 | 13 |
| hsa-miR-885-5p | −1.8 | 4.7E−03 | 2.8E−01 | 15 | 28 |
| hsa-miR-652 | −1.7 | 2.0E−03 | 1.9E−01 | 456 | 756 |
| hsa-miR-1281 | −1.6 | 3.5E−02 | 5.4E−01 | 128 | 209 |
| hsa-miR-4310 | −1.6 | 2.0E−02 | 4.6E−01 | 5 | 9 |
| hsa-miR-4800-3p | −1.6 | 2.4E−02 | 4.8E−01 | 22 | 35 |
| hsa-miR-4727-3p | −1.6 | 3.3E−03 | 2.3E−01 | 4 | 6 |
| hsa-miR-4791 | −1.5 | 1.7E−02 | 4.3E−01 | 4 | 6 |
| hsa-miR-505* | 1.5 | 6.3E−03 | 2.9E−01 | 48 | 32 |
| hsa-miR-3651 | 1.6 | 4.3E−03 | 5.7E−01 | 50 | 32 |
| hsa-miR-543 | 1.6 | 5.7E−03 | 2.8E−01 | 4 | 2 |
| hsa-miR-23a* | 1.6 | 2.3E−03 | 1.9E−01 | 83 | 52 |
| hsa-miR-18a | 1.6 | 2.3E−03 | 1.9E−01 | 74 | 46 |
| hsa-miR-1246 | 1.6 | 1.9E−02 | 4.5E−01 | 148 | 92 |
| hsa-miR-3615 | 1.6 | 3.1E−02 | 5.0E−01 | 14 | 9 |
| hsa-miR-4484 | 1.6 | 1.3E−02 | 4.0E−01 | 166 | 102 |
| hsa-miR-4800-5p | 1.6 | 7.8E−03 | 3.3E−01 | 5 | 3 |
| hsa-miR-629* | 1.6 | 3.8E−02 | 5.6E−01 | 13 | 8 |
| hsa-miR-30e* | 1.7 | 3.5E−02 | 5.5E−01 | 9 | 5 |
| hsa-miR-24-2* | 1.7 | 1.9E−03 | 1.9E−01 | 52 | 31 |
| hsa-miR-18b | 1.7 | 1.9E−02 | 4.5E−01 | 6 | 3 |
| hsa-miR-4667-5p | 1.7 | 2.1E−02 | 4.6E−01 | 7 | 4 |
| hsa-miR-483-5p | 1.7 | 1.7E−02 | 4.3E−01 | 5 | 3 |
| hsa-miR-27b* | 1.7 | 8.3E−03 | 3.3E−01 | 53 | 31 |
| hsa-miR-629 | 1.7 | 8.0E−04 | 1.1E−01 | 45 | 26 |
| hsa-miR-187 | 1.7 | 4.0E−02 | 5.6E−01 | 21 | 12 |
| hsa-miR-487a | 1.7 | 1.8E−02 | 4.4E−01 | 6 | 3 |
| hsa-miR-1244 | 1.8 | 2.3E−02 | 4.7E−01 | 4 | 2 |
| hsa-miR-132 | 1.8 | 3.2E−05 | 1.4E−02 | 332 | 186 |
| hsa-miR-550a* | 1.8 | 6.0E−03 | 2.9E−01 | 9 | 5 |
| hsa-miR-4286 | 1.8 | 2.8E−02 | 4.8E−01 | 12 | 7 |
| hsa-miR-542-5p | 1.9 | 9.5E−03 | 3.4E−01 | 6 | 3 |
| hsa-let-7i* | 1.9 | 1.4E−02 | 4.1E−01 | 7 | 3 |
| hsa-miR-625 | 1.9 | 6.0E−03 | 2.9E−01 | 44 | 24 |
| hsa-miR-411 | 2.0 | 2.5E−02 | 4.8E−01 | 7 | 3 |
| hsa-miR-3175 | 2.0 | 4.4E−03 | 2.7E−01 | 10 | 5 |

TABLE 1-continued

List of the 60 modulated mature microRNAs (|fold| ≥ 1.5 and raw p-value ≤ 0.05) in LS vs NLS differential analysis (Blume acne study: GRDS0051) starting with 3391 Affymetrix identifiers

| Affymetrix id | Fold Change | RawPValue | FDR_BH | mean expression LS | mean expression NLS |
|---|---|---|---|---|---|
| hsa-miR-192 | 2.0 | 2.8E−02 | 4.8E−01 | 12 | 6 |
| hsa-miR-503 | 2.0 | 2.2E−02 | 4.7E−01 | 8 | 4 |
| hsa-miR-31 | 2.1 | 6.2E−03 | 2.9E−01 | 445 | 215 |
| hsa-miR-1301 | 2.1 | 7.4E−03 | 3.2E−01 | 19 | 9 |
| hsa-miR-92a-1* | 2.1 | 5.1E−03 | 2.8E−01 | 24 | 12 |
| hsa-miR-501-5p | 2.2 | 6.0E−04 | 9.4E−02 | 18 | 8 |
| hsa-miR-4732-5p | 2.2 | 2.5E−03 | 1.9E−01 | 28 | 13 |
| hsa-miR-150 | 2.2 | 2.0E−04 | 4.9E−02 | 932 | 423 |
| hsa-miR-424* | 2.2 | 4.2E−03 | 2.7E−01 | 19 | 9 |
| hsa-miR-4417 | 2.3 | 1.7E−03 | 1.8E−01 | 24 | 10 |
| hsa-miR-4521 | 2.3 | 7.0E−05 | 1.8E−02 | 210 | 90 |
| hsa-miR-365* | 2.4 | 4.0E−04 | 6.3E−02 | 27 | 11 |
| hsa-miR-181a* | 2.4 | 1.2E−03 | 1.5E−01 | 10 | 4 |
| hsa-miR-155 | 3.1 | 3.6E−07 | 4.0E−04 | 720 | 234 |
| hsa-miR-27a* | 3.1 | 6.0E−04 | 8.8E−02 | 52 | 17 |
| hsa-miR-941 | 3.2 | 5.3E−05 | 1.6E−02 | 14 | 4 |
| hsa-miR-146b-3p | 3.4 | 2.7E−05 | 1.3E−02 | 9 | 3 |
| hsa-miR-146b-5p | 3.7 | 1.0E−07 | 2.0E−04 | 208 | 56 |
| hsa-miR-29b-1* | 3.8 | 7.0E−05 | 1.8E−02 | 16 | 4 |
| hsa-miR-421 | 4.2 | 2.5E−05 | 1.3E−02 | 22 | 5 |
| hsa-miR-21 | 4.7 | 7.9E−05 | 1.9E−02 | 22 | 5 |
| hsa-miR-212 | 5.3 | 8.0E−07 | 7.0E−04 | 18 | 3 |
| hsa-miR-21* | 10.0 | 1.3E−07 | 2.0E−04 | 28 | 3 |
| hsa-miR-223 | 15.0 | 2.6E−06 | 1.8E−03 | 99 | 7 |

Note:
When the FDR value is highlighted in bold, then FDR ≤ 0.05
A biomarker should preferably be strongly expressed in the pathology and weakly or not expressed in healthy individuals. Based on both fold modulation (the highest possible) and expression in healthy skin (the lowest possible), a list of 11 potential biomarkers of acne was established. This list comprises the microRNAs: hsa-miR-223, hsa-miR-21*, hsa-miR-212, hsa-miR-21, hsa-miR-421, hsa-miR-29b-1*, hsa-miR-146b-5p, hsa-miR-146b-3p, hsa-miR-941, hsa-miR-27a* and hsa-miR-155.

A biomarker should preferably be strongly expressed in the pathology and weakly or not expressed in healthy individuals. Based on both fold modulation (the highest possible) and expression in healthy skin (the lowest possible), a list of 11 potential biomarkers of acne was established. This list comprises the microRNAs: hsa-miR-223, hsa-miR-21*, hsa-miR-212, hsa-miR-21, hsa-miR-421, hsa-miR-29b-1*, hsa-miR-146b-5p, hsa-miR-146b-3p, hsa-miR-941, hsa-miR-27a* and hsa-miR-155 (shown in the box above).

Materials and Methods
Total RNA Extraction (mRNA and microRNAs)

Total RNA extraction was performed beforehand in order to carry out a transcriptome study. This extraction was performed with the miRNeasy Mini Kit from QIAGEN which extracts large RNAs (mRNA) as well as small RNAs including microRNAs. This kit comprises three successive steps: lysing tissues to release RNAs contained in cells, isolating RNAs on a membrane, then eluting them. The results of the transcriptome study previously established were used for the biological interpretation of the data on the obtained microRNAs.

Large-Scale Study of microRNAs
Study of microRNA Gene Expression: Affymetrix miRNA Chip The miRNA 3.0 chip consists of nucleic acid fragments, called probes, bound to a physical substrate and whose sequence set corresponds to the microRNAs of 153 organisms including more than 1700 mature forms of human microRNAs. Each probe (single-stranded DNA fragment) is complementary to a given microRNA. For each microRNA, several probes, sometimes varying by a few base pairs, are present on the chip. This is called a probe set. The miRNA 3.0 chip contains nearly 20,000 probe sets of which more than 5600 are specific to small human RNAs, including microRNAs (1733 matures and 1658 precursors). The design of this chip was based on miRBase version 17. A probe set dedicated to a mature microRNA is composed of 9 identical probes, complementary to the sequence of the target mature RNA.

The experiment is carried out starting with 300 ng of total RNA. The first step consists in adding a poly(A) tail to the microRNAs. This poly(A) tail, initially present on the mRNAs and thereafter also on the microRNAs, will allow the binding of the 3DNA® molecule labeled with 15 biotins. The result is the formation of biotinylated RNAs. The second step is the hybridization of the RNAs to their respective probes; as the probes present in the various compartments of the chip are specific to microRNAs, biotinylated mRNAs are excluded while biotinylated microRNAs hybridize to the probes. Washing eliminates the molecules which are not hybridized to the chip. In a third step, streptavidin coupled to a fluorescent molecule, phycoerythrin, is added. Thanks to its affinity for biotin, streptavidin makes it possible to detect biotinylated microRNAs. To optimize this labeling, an amplification of the labeling is performed: to this end, a goat anti-streptavidin antibody coupled to biotin is introduced. This last will bind to the preceding biotinylated microRNA-streptavidin/phycoerythrin complex. A second addition of streptavidin/phycoerythrin will have the effect of amplifying the fluorescent label to improve detection. The successive labeling and washing steps are automated thanks to a dedicated Affymetrix platform. The fluorescent signal is then processed by means of the Expression Console Software, provided by Affymetrix. The greater the quantity of microRNA bound to its complementary probe, the stronger the light signal. Thus, for each chip, it is by comparing the light intensity corresponding to each probe of a treated sample versus a control sample that the effect of this treatment on gene expression can be analyzed.

Biostatistics

From a technical perspective, transcriptome studies are both reliable and affordable. However, analysis of the large amounts of data generated remains a crucial point. In this area, resorting to bioinformatic tools and biostatistics is essential. There remains no consensus concerning the choice of mathematical algorithms used to treat these data. For miRNome studies in particular, whether on a large scale or a smaller scale by qPCR, several methods for normalizing raw data have been proposed. Concerning large-scale studies of microRNA expression, the most commonly used method today is RMA normalization. Before normalization, the expression data are transformed to $\log_2$ to produce a linear range and to reduce the extent of the data.

Array Studio software: Array Studio is a software package designed for biologists and bioinformatics scientists to statistically analyze new-generation sequencing data, SNPs or microarrays. It includes in particular support for all microarray platforms, including Agilent, Illumina and Affymetrix, the latter being used in the context of our study. First, it makes it possible to normalize raw data by various methods and, second, to carry out differential intergroup analyses to compare microRNA expression profiles.

Robust Multiarray/Multichip Average (RMA) normalization: Large-scale studies now make it possible to analyze the expression profiles of numerous genes in a single experiment; for example, to characterize an individual's miRNome. These experiments, repeated for each sample (individual) tested, generate a great deal of data but these data may be biased by technological variations. The goal of normalization is to remove technology-related noise in order to take biological variations into account as precisely as possible. RMA normalization comprises three successive steps: background noise correction; quantile normalization: carried out on all the chips of the study concerned and tends to homogenize expression level distributions between chips in order to analyze them jointly or to compare them; and "median polish": the step during which the fluorescence intensities of targets binding to the same probe set are combined in order to estimate a single intensity value, per chip, for each target set (or gene).

Differential Analyses

Characterization of the miRNome in a pathological condition is achieved by comparison with the microRNA profiles obtained in a healthy condition. The principle of this comparison rests on the calculation of fold modulation (change in gene expression level). To know the confidence level given to this fold, a p-value is associated therewith, calculated using a hypothesis test called Student's t-test.

Calculation of Fold Modulation a) Relative Expression of Large-Scale Data (Affymetrix)

Since the normalized expression data were transformed to $\log_2$, relative expression is calculated as follows:

Relative expression=$2^\Delta$ with $\Delta=\log_2$(Mean expression$_{gene\ i\ condition\ B}$)–$\log_2$(Mean expression$_{gene\ i\ condition\ A/reference}$)

b) Modulation Factor or "Fold"

Fold modulation is expressed as the change in the mean expression of gene i in condition A (reference) relative to condition B; if the fold modulation is positive then gene i is overexpressed in condition A relative to control condition B. Conversely, if the fold modulation is negative then gene i is underexpressed in condition A relative to control condition B. If the calculated relative expression value is greater than 1, it is equivalent to a positive fold change. On the other hand, if the calculated relative expression is between 0 and 1, meaning that the gene is expressed more in the reference condition (A) than in the test condition (B), the operation −1/fold is then carried out to obtain negative fold change values, which are more easily interpretable. A fold threshold may be set by the biologist to specifically select those having biological interest; in this study, it is set at +/−1.5.

Principle of a Hypothesis Test

In statistics, a hypothesis test consists in evaluating a statistical hypothesis with respect to a data set (sample). For example, if one asks the question: Is gene i differentially expressed in condition A relative to condition B? Condition A may correspond to affected individuals and condition B to healthy control individuals.

To answer yes or no to the question involves deciding between two hypotheses:

The null hypothesis (H0): the gene is not differentially expressed,

The alternative hypothesis (H1): the gene is differentially expressed.

Two types of errors may arise:

A type I error: rejecting H0 when H0 is true, amounts to considering that the gene is differentially expressed when it is not; this is a false-positive.

A type II error: not rejecting H0 when H0 is false, amounts to considering that the gene is not differentially expressed when it actually is; this is a false-negative.

The maximum tolerated risk (denoted $\alpha$) is called the significance threshold; it is generally set at 0.05. In our example, that amounts on average to accepting the risk of being mistaken 5 times out of 100 and thus accepting on average 5% false-positives in our analysis.

The test statistic is calculated from the data. Its value makes it possible to estimate the probability (p-value) necessary to obtain these data if H0 is true. As a function of the significance threshold set beforehand and this p-value, the decision to reject or not to reject H0 may be made.

Student's Test or t-Test

This test makes it possible to evaluate whether the expression means of gene i in each condition A and B are statistically different from each other and thus to compare one condition relative to another. The p-value of the t-test then makes it possible to conclude whether the difference between the averages is not due to chance:

If the p-value ≤0.05 then H0 is rejected; the averages of the two conditions A and B are said to be significantly different, gene i is thus modulated significantly in condition A relative to condition B.

If the p-value >0.05 then H0 is not rejected; the averages of the two conditions A and B are said to be not significantly different, gene i is thus not modulated significantly in condition A relative to condition B.

Control of False Discovery Rate (FDR)

Expression chips for large-scale analyses make it possible to simultaneously measure the transcriptional activity of several thousand genes for a given biological sample. To analyze them simultaneously, the hypothesis tests are multiplied. However, when the tests are multiplied, the probability of detecting a significantly modulated gene, when it is not, increases. To control the false discovery rate (genes considered modulated when they are not), the false discovery rate is controlled using a method developed by Benjamini and Hochberg 1995, Journal of the Royal Statistical Society. Series B (Methodological) vol. 57, No. 1 (1995), pp. 289-300—the false discovery rate (FDR)—which corrects p-values associated with t-tests in order to retain the same false discovery rate irrespective of the number of genes. In conclusion, after a differential analysis, gene i is considered significantly modulated if it meets two conditions:

|fold|≥1.5
FDR<0.05

The invention claimed is:

1. A method of treating a human subject for acne, comprising:

(a) assaying a dermis sample from a subject for expression levels of the following microRNAs: hsa-miR-223, hsa-miR-21*, hsa-miR-212, hsa-miR-21, hsa-miR-421, hsa-miR-29b-1*, hsa-miR-146b-5p, hsa-miR-146b-3p, hsa-miR-941, hsa-miR-27a* and hsa-miR-155

(c) diagnosing based on the assaying that the subject having a higher than 3-fold increase in the expression level of all of the miRNAs compared to the expression level of all the same miRNAs in a control sample from a healthy subject as suffering from acne or likely to suffer from acne; and (b) administering to the subject a molecule or a combination of molecules that decreases the expression or activity of one or more of hsa-miR-223, hsa-miR-21*, hsa-miR-212, hsa-miR-21, hsa-miR-421, hsa-miR- 29b-1*, hsa-miR-146b-5p, hsa-miR-146b-3p, hsa-miR-941, hsa-miR-27a* and hsa-miR-155 in a dermis sample from the subject compared to the expression level of all the same miRNAs in a control sample from a healthy subject.

2. The method according to claim 1, further comprising determining in a sample from said subject the expression of at least one microRNA selected from the group consisting of hsa-miR-617, hsa-miR-885-5p, hsa-miR-652, hsa-miR-1281, hsa-miR-4310, hsa-miR-4800-3p, hsa-miR-4727-3p, hsa-miR-4791, hsa-miR-505*, hsa-miR-3651, hsa-miR-543, hsa-miR-23a*, hsa-miR-18a, hsa-miR-1246, hsa-miR-3615, hsa-miR-4484, hsa-miR-4800-5p, hsa-miR-629*, hsa-miR-30e*, hsa-miR-24-2*, hsa-miR-18b, hsa-miR-4667-5p, hsa-miR-483-5p, hsa-miR-27b*, hsa-miR-629, hsa-miR-187, hsa-miR-487a, hsa-miR-1244, hsa-miR-132, hsa-miR-550a*, hsa-miR-4286, hsa-miR-542-5p, hsa-let-7i*, hsa-miR-625, hsa-miR-411, hsa-miR-3175, hsa-miR-192, hsa-miR-503, hsa-miR-31, hsa-miR-1301 hsa-miR-92a-1*, hsa-miR-501-5p, hsa-miR-4732-5p, hsa-miR-150, hsa-miR-424*, hsa-miR-4417, hsa-miR-4521, hsa-miR-365* and hsa-miR-181 a*.

3. The method according to claim 1, further comprising additionally determining in a sample from said subject the expression of one or more microRNAs selected from the group consisting of hsa-miR-617, hsa-miR-885-5p, hsa-miR-652, hsa-miR-1281, hsa-miR-4310, hsa-miR-4800-3p, hsa-miR-4727-3p and hsa-miR-4791, wherein a decrease in the expression of one or more of these microRNAs in the sample relative to the controls indicates that the subject suffers from or is likely to suffer from acne.

4. The method according to claim 1, further comprising determining in a sample from said subject the expression of one or more microRNAs selected from the group consisting of hsa-miR-505*, hsa-miR-3651, hsa-miR-543, hsa-miR-23a*, hsa-miR-18a, hsa-miR-1246, hsa-miR-3615, hsa-miR-4484, hsa-miR-4800-5p, hsa-miR-629*, hsa-miR-30e*, hsa-miR-24-2*, hsa-miR-18b, hsa-miR-4667-5p, hsa-miR-483-5p, hsa-miR-27b*, hsa-miR-629, hsa-miR-187, hsa-miR-487a, hsa-miR-1244, hsa-miR-132, hsa-miR-550a*, hsa-miR-4286, hsa-miR-542-5p, hsa-let-7i*, hsa-miR-625, hsa-miR-411, hsa-miR-3175, hsa-miR-192, hsa-miR-503, hsa-miR-31, hsa-miR-1301 hsa-miR-92a-1*, hsa-miR-501-5p, hsa-miR-4732-5p, hsa-miR-150, hsa-miR-424*, hsa-miR-4417, hsa-miR-4521, hsa-miR-365*, hsa-miR-181a*, hsa-miR-155, hsa-miR-27a*, hsa-miR-941, hsa-miR-146b-3p, hsa-miR-146b-5p, hsa-miR-29b-1*, hsa-miR-421, hsa-miR-21, hsa-miR-212, hsa-miR-21* and hsa-miR-223.

5. The method of claim 1, wherein the molecule or combination of molecules comprises an anti-seborrheic, an anti-infective, or a combination thereof.

6. The method of claim 1, wherein the molecule or a combination of molecules comprises benzoyl peroxide, a retinoid, or a naphthoic acid derivative.

7. The method of claim 6, wherein the napthoic acid derivative is 6-[3-(1-adamantyl)-4-methoxyphenyl]-2-naphthoic) acid (adapalene).

* * * * *